United States Patent [19]

Schwan

[11] 3,940,400

[45] Feb. 24, 1976

[54] 3-METHYL-4-PHENYL-1,2,3,4-TETRAHYDROBENZ[G]ISOQUINOLINE HYDROBROMIDE

[75] Inventor: Thomas J. Schwan, Norwich, N.Y.

[73] Assignee: Morton-Norwich Products, Inc., Norwich, N.Y.

[22] Filed: Nov. 14, 1974

[21] Appl. No.: 523,590

[52] U.S. Cl........ 260/286 R; 260/283 R; 260/570.9; 424/258
[51] Int. Cl.$^2$.......................................... C07D 217/08
[58] Field of Search....... 260/286 R, 283 R, 283 SY

[56] References Cited
UNITED STATES PATENTS 3,639,411 2/1972 Albertson........................ 260/286 R
3,790,576 2/1974 DeWald .......................... 260/286 R

OTHER PUBLICATIONS

Iwai et al., "Chem. Pharm. Bull." (Tokyo) II, 12, 1556–1563, (1963).

Primary Examiner—Richard J. Gallagher
Assistant Examiner—David E. Wheeler
Attorney, Agent, or Firm—Anthony J. Franze

[57] ABSTRACT

A compound 3-methyl-4-phenyl-1,2,3,4-tetrahydrobenz[g]isoquinoline hydrochloride of the formula possesses pharmacological activity as an antianxiety agent.

1 Claim, No Drawings

3-METHYL-4-PHENYL-1,2,3,4-TETRAHYDROBENZ[G]ISOQUINOLINE HYDROBROMIDE

This invention relates to a chemical compound. In particular it is concerned with a compound of the formula:

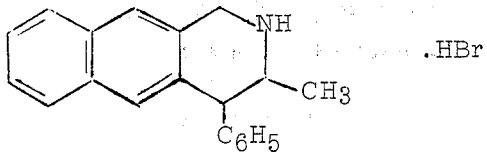

possessing pharmacological activity affecting the central nervous system. When administered perorally to animals, it exhibits antianxiety activity. Such antianxiety action is evidenced in the control of pentylenetetrazol induced tonic extensor seizures in mice. An oral dose of 50 mg/kg of this compound to mice intravenously receiving 45 mg/kg of pentylenetetrazol counteracts this property of pentylenetetrazol.

In order that this invention may be readily available to and understood by those skilled in the art, the following example is supplied.

A.
2-(1-Bromo-2-naphthylmethylamino)-1-phenyl-1-propanol hydrochloride

A mixture of 38.4 g (0.164 mole) 1-bromo-2-naphthaldehyde, 16.4g (0.164 mole) triethylamine, and 30.6 g (0.164 mole) of 2-amino-1-phenyl-1-propanol hydrochloride in 500 ml $CH_3OH$ was stirred and refluxed for 60 minutes, then cooled to 10°–20° while 6.23 g (0.164 mole) of sodium borohydride was added over 5 minutes. The reaction mixture was stirred at ambient temperature (15°–21°) for 60 minutes and diluted with 500 ml $H_2O$. The mixture was stirred for 15 minutes and extracted with 2 × 350 ml $CHCl_3$. The combined extracts were dried ($MgSO_4$) and concentrated to dryness in vacuo to give 59.6 g (99%) of the free base.

Treatment of a 13.6 g (0.0368 mole) sample of the free base dissolved in 50 ml ethanol with 35 ml ethanolic hydrogen chloride gave 9.84 g (66%) of the product, m.p. 234°–237°. An analytical sample, m.p. 233°–236°, was obtained by drying a portion of the above sample at 100° over NaOH in vacuo.

Anal. Calcd. for $C_{20}H_{20}BrNO \cdot HCl$: C, 59.05; H, 5.21; N, 3.44. Found: C, 58.71; H, 5.23; N, 3.47.

B.
10-Bromo-3-methyl-4-phenyl-1,2,3,4-tetrahydrobenz[g]isoquinoline hydrobromide A mixture of 74.0 g (0.175 mole) of the free base of A and 293 g polyphosphoric acid was stirred at 90°–95° on a steam bath for 22 hours. The mixture was cooled and poured into 1500 ml cold, stirred tap water. After a 30 minute stirring period, the solid was filtered thru a coarse sintered glass funnel. The wet solid was stirred with a mixture of 1000 ml $H_2O$ and 300 ml $CH_3OH$. KOH (84 g) was added to pH 10. The mixture was extracted with 500 ml $CHCl_3$ followed by 150 ml $CHCl_3$. The combined extracts were dried ($MgSO_4$) and concentrated to dryness in vacuo to an oil. Treatment of an ethanolic solution of the oil with 50 ml of 48% HBr gave in three crops 66.9 g (88.4%) of the product.

Anal. Calcd. for $C_{20}H_{18}BrN \cdot HBr$: C, 55.45; H, 4.42. Found: C, 55.06; H, 4.30.

C.
3-Methyl-4-phenyl-1,2,3,4-tetrahydrobenz[g]isoquinoline hydrobromide A mixture of 5.65 g (0.013 mole) of B, 2.0 g 5% Pd/C (50% moisture), and 150 ml $CH_3OH$ was shaken in the presence of hydrogen for 16 hours. The mixture was filtered and the catalyst was washed with 2 × 75 ml hot dimethylformamide. The filtrate and combined washings were concentrated to dryness in vacuo. The residue was boiled with 100 ml $CH_3CN$ for 15 minutes, cooled overnight, and filtered to give 4.10 g (89%) of the product.

An analytical sample, m.p. 208°–9°, was obtained by recrystallization from methanol.

Anal. Calcd. for $C_{20}H_{19}N \cdot HBr$: C, 67.80; H, 5.65; N, 3.92. Found: C, 67.71; H, 5.57; N, 3.91.

What is claimed is:
1. A compound of the formula:

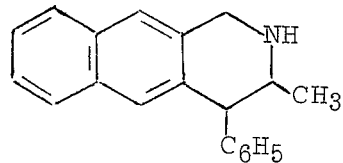

* * * * *